(12) United States Patent
Murray et al.

(10) Patent No.: US 7,193,093 B2
(45) Date of Patent: Mar. 20, 2007

(54) PROCESS FOR PRODUCING ALKYLENE OXIDE

(75) Inventors: Brendan Dermot Murray, Houston, TX (US); Garo Garbis Vaporciyan, Houston, TX (US)

(73) Assignee: Shell Oil Company, Houston, TX (US)

( * ) Notice: Subject to any disclaimer, the term of this patent is extended or adjusted under 35 U.S.C. 154(b) by 25 days.

(21) Appl. No.: 10/872,849

(22) Filed: Jun. 21, 2004

(65) Prior Publication Data

US 2005/0020840 A1     Jan. 27, 2005

Related U.S. Application Data

(60) Provisional application No. 60/483,709, filed on Jun. 30, 2003.

(51) Int. Cl.
C07D 301/19     (2006.01)

(52) U.S. Cl. ..................................... 549/529

(58) Field of Classification Search ............ 549/529
See application file for complete search history.

(56) References Cited

U.S. PATENT DOCUMENTS

| | | | |
|---|---|---|---|
| 3,350,422 A | 10/1967 | Kollar | 260/348.5 |
| 3,351,635 A | 11/1967 | Kollar | 260/348.5 |
| 3,434,975 A | 3/1969 | Sheng et al. | |
| 3,453,218 A | 7/1969 | Sheng et al. | |
| 3,480,563 A | 11/1969 | Bonetti et al. | |
| 4,242,530 A | 12/1980 | Smith, Jr. | |
| RE30,642 E | 6/1981 | Becker | |
| 4,410,501 A | 10/1983 | Taramasso et al. | |
| 4,443,559 A | 4/1984 | Smith, Jr. | |
| 4,590,172 A | 5/1986 | Isaacs | |
| 4,593,012 A | 6/1986 | Usui et al. | |
| 4,607,113 A | 8/1986 | Shum et al. | |
| 4,661,463 A | 4/1987 | Mocella | |
| 4,666,692 A | 5/1987 | Taramasso et al. | |
| 4,687,868 A | 8/1987 | Shum et al. | |
| 4,701,428 A | 10/1987 | Bellussi et al. | |
| 4,772,731 A | 9/1988 | Shum et al. | |
| 4,822,936 A | 4/1989 | Maurer et al. | |
| 5,017,712 A | 5/1991 | Usui et al. | |
| 5,266,546 A | 11/1993 | Hearn | |
| 5,348,710 A | 9/1994 | Johnson et al. | |
| 5,475,159 A | 12/1995 | Singleton et al. | |
| 5,905,178 A | 5/1999 | Hildreth | 585/258 |
| 6,323,147 B1 | 11/2001 | Yamamoto et al. | |
| 6,455,712 B1 | 9/2002 | Vaporciyan et al. | |

FOREIGN PATENT DOCUMENTS

| | | |
|---|---|---|
| EP | 58473 | 9/1985 |
| EP | 100119 | 9/1986 |
| EP | 230949 | 7/1992 |
| EP | 345856 | 8/1992 |
| EP | 1209155 | 5/2002 |
| EP | 1243585 A1 | 9/2002 |
| ES | 2165771 | 3/2002 |
| GB | 2071071 | 9/1981 |
| JP | 01100136 | 4/1989 |
| NL | 1010372 | 5/1999 |
| WO | 01/56693 | 8/2001 |
| WO | 01/70714 | 9/2001 |
| WO | WO 02/48125 A2 | 6/2002 |
| WO | WO 02072507 | 9/2002 |
| WO | WO 03027087 | 4/2003 |

OTHER PUBLICATIONS

Podrebarac. G.G. et al. "More Uses for Catalytic Distillation." ChemTech. Washington, DC. vol. 27. No. 5. May 1997. pp. 37-45.
International Search Report, dated Feb. 15, 2005.

*Primary Examiner*—Amelia A. Owens

(57) ABSTRACT

A process for preparing an alkylene oxide, which process comprises:
(i) oxidizing an alkylbenzene to obtain a stream comprising alkylbenzene hydroperoxide,
(ii) contacting at least part of the alkylbenzene hydroperoxide obtained in step (i) with an olefin to obtain a product stream comprising an alkylene oxide
(iii) separating alkylene oxide compound from the product stream of step (ii) to obtain (a) a residual product stream comprising alkylphenyl alcohol, and (b) alkylene oxide,
(iv) feeding at least a part of the residual product stream comprising alkylphenyl alcohol to a reactor having a catalytic distillation zone, and concurrently in the reactor,
(a) contacting the residual product stream comprising alkylphenyl alcohol with hydrogen in the catalytic distillation zone to convert the alkylphenyl alcohol in the residual product stream to alkylbenzene and form a reaction mixture, and
(b) separating alkylbenzene from the reaction mixture by fractional distillation,
(v) withdrawing a stream comprising alkylbenzene and having a reduced concentration of alkylphenyl alcohol than the feed stream from the reactor at a position upper from the catalytic reaction zone;
(vi) withdrawing from the reactor at a position lower than the catalytic distillation zone a bottom stream comprising dimer(s) of alkylbenzene;
(vii) converting the dimer(s) of alkylbenzene in the bottom stream from (vi) to alkylbenzene; and
(viii) recycle at least a part of the alkylbenzene produced from (iv)(b) and/or (vi) to step (i).

23 Claims, No Drawings

PROCESS FOR PRODUCING ALKYLENE OXIDE

This application claims the benefit of U.S. Provisional Application No. 60/483,709 filed Jun. 30, 2003, the entire disclosure of which is hereby incorporated by reference.

FIELD OF THE INVENTION

The present invention relates to an improved process for producing alkylene oxide by epoxidizing an olefin using an organic hydroperoxide.

BACKGROUND OF THE INVENTION

Many different methods for the preparation of alkylene oxides have been developed. One such method involves the epoxidation of an olefin in a liquid phase reaction using an organic hydroperoxide as the oxidizing agent. NL-C-1010372 describes a process comprising reacting propene with ethylbenzene hydroperoxide to obtain propylene oxide and 1-phenyl ethanol. The 1-phenyl ethanol is subsequently dehydrated to obtain styrene, which is a useful starting material for other chemical reactions.

WO01/70714, assigned to Sumitomo, describes a process relating to oxidizing isopropylbenzene (also known as "cumene") to obtain isopropylbenzene peroxide as an oxygen carrier for the epoxidation of propylene to produce propylene oxide and isopropylbenzene alcohol (cumyl alcohol). The isopropylphenyl alcohol is dehydrated/hydrogenated, via a hydrogenolysis step, to isopropylbenzene (cumene) and recycled for repeated use without the co-production of styrene. During the hydrogenolysis step, substantial quantities of i-propylcyclohexane and cumene dimer are produced as undesirable by-products, due to the hydrogenation or dimerization of cumene and alpha-methyl styrene which remain on the hydrogenation bed after being produced.

U.S. Pat. No. 6,455,712, assigned to Shell, describes a process for producing alkylene oxide (also known as oxirane) compounds, such as propylene oxide, by oxidizing olefin with alkylbenzene hydroperoxide obtained by oxidizing alkylbenzene with oxygen. The alkylbenzene hydroperoxide is converted to alkylphenyl alcohol which is dehydrated and hydrogenated, followed by fractionation, to separate alkylbenzene from other side products for reuse for making alkylbenzene hydroperoxide. Substantial quantities of alkylphenyl alcohol could be converted to alkylcyclohexane and/or dimers/oligomers of alkylbenzene as side products.

It is therefore desirable to develop a more efficient process which would combine multiple process steps for converting alkylphenyl alcohol to alkylbenzene and fractionation into fewer steps and yet accumulate fewer undesirable side products of alkylbenzene, such as dimers/oligomers and alkylcyclohexane, to minimize loss of alkylbenzene utilized.

SUMMARY OF THE INVENTION

The invention is directed to a process for preparing an alkylene oxide, which process comprises:
(i) oxidizing an alkylbenzene to obtain a stream comprising alkylbenzene hydroperoxide;
(ii) contacting at least part of the alkylbenzene hydroperoxide obtained in step (i) with an olefin to obtain a product stream comprising an alkylene oxide;
(iii) separating alkylene oxide compound from the product stream of step (ii) to obtain (a) a residual product stream comprising alkylphenyl alcohol and (b) alkylene oxide; and,
(iv) feeding at least a part of the residual product stream comprising alkylphenyl alcohol to a reactor having a catalytic distillation zone, and concurrently in the reactor:
  (a) contacting the residual product stream comprising alkyphenyl alcohol with hydrogen in the catalytic distillation zone to convert the alkylphenyl alcohol in the residual product stream to alkylbenzene and form a reaction mixture; and,
  (b) separating alkylbenzene from the reaction mixture by fractional distillation.
(v) withdrawing a stream comprising alkylbenzene and having a reduced concentration of alkylphenyl alcohol than the feed stream from the reactor at a position above the catalytic reaction zone;
(vi) withdrawing from the reactor at a position lower than the catalytic distillation zone a bottom stream comprising dimer(s) of alkylbenzene;
(vii) converting the dimer(s) of alkylbenzene in the bottom stream from (vi) to alkylbenzene; and
(viii) recycling at least a part of the alkylbenzene produced from (iv)(b) and/or (vi) to step (i).

DETAILED DESCRIPTION OF THE INVENTION

It has now been found that the process of the present invention enables efficient epoxidation of an olefin by combining multiple process steps for converting alkylphenyl alcohol to alkylbenzene for reuse as an oxygen carrier, and also accumulates fewer undesirable side products of alkylbenzene, such as dimers/oligomers and alkylcyclohexane. Furthermore, as a particular embodiment of the present invention, dimers/oligomer of alkylbenzene produced during the process are cracked to alkylbenzene and recycled for reuse, and the loss of alkylbenzene is thereby minimized.

As represented in Pathway I below, the present process utilizes alkylbenzene hydroperoxide as an epoxidizing agent to produce an alkylene oxide from an olefin. The alkylbenzene hydroperoxide is converted to alkylphenyl alcohol during the epoxidation process, and the alkylene oxide is separated from the reaction product to obtain a residual product stream comprising alkylphenyl alcohol (also known as alkylbenzyl alcohol), alkylbenzene and optionally alkenylbenzene. The residual product stream is dehydrated and hydrogenated to convert alkylphenyl alcohol to alkylbenzene. Preferably, the dehydration/hydrogenation reaction is accomplished by feeding the residual product stream to a catalytic fractional distillation reactor to be contacted with fixed bed catalytic packing in the catalytic distillation zone in order to concurrently carry out a one-step dehydration-hydrogenation reaction, fractionate and remove the lower boiling point alkylbenzene produced in the catalytic distillation zone by distillation before it is converted to alkylcyclohexane or dimers of alkylphenyl alcohol. Unconverted alkylphenyl alcohol or alkenylbenzene continues to be refluxed to the catalytic distillation zone until being converted to alkylbenzene. A heating device with heating media may be utilized to provide the heat needed for the distillation reaction.

As a particular embodiment of the present invention, heavy dimers or polymers of alkylbenzenes, such as cumene dimers, made in the catalytic distillation mode having higher boiling points than alkylbenzenes and alkylphenyl alcohols fall to the bottom of the catalytic distillation reactor. The dimers or polymers in the bottom of the reactor may be hydrocracked at the bottom of the reactor or can be withdrawn as a part of the bottom stream of the catalytic distillation reactor and sent to a hydrocracking reactor to be hydrogenated, e.g., in a fixed bed mode, to produce more alkylbenzenes, such as cumene.

As a particular embodiment of the present invention, the bottom stream of the catalytic distillation reactor may be sent to a flasher or a distillation column wherein alkylbenzene, alkylphenyl alcohol and alkenyl benzene (such as alpha-methyl styrene) are separated out from alkylbenzene dimers/oligomers, and recycled back to the catalytic distillation reactor. The heavier alkylbenzene dimers/oligomers are then sent to a reactor for hydrocracking to recover alkylbenzene. Non-limiting illustrative examples of side product dimers made from the dimerization of cumene include 2,3-dimethy-2,3-diphenyl butane and 2-methyl-2,4-diphenylpentane (See Pathway II).

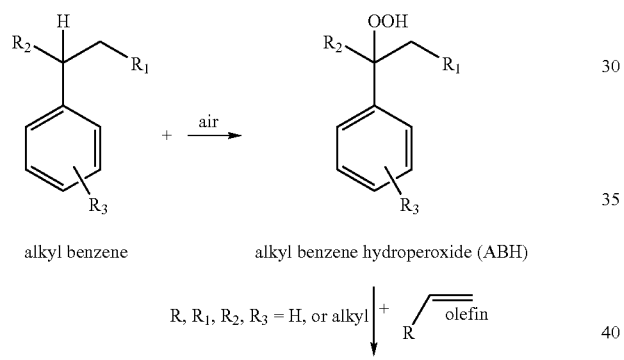

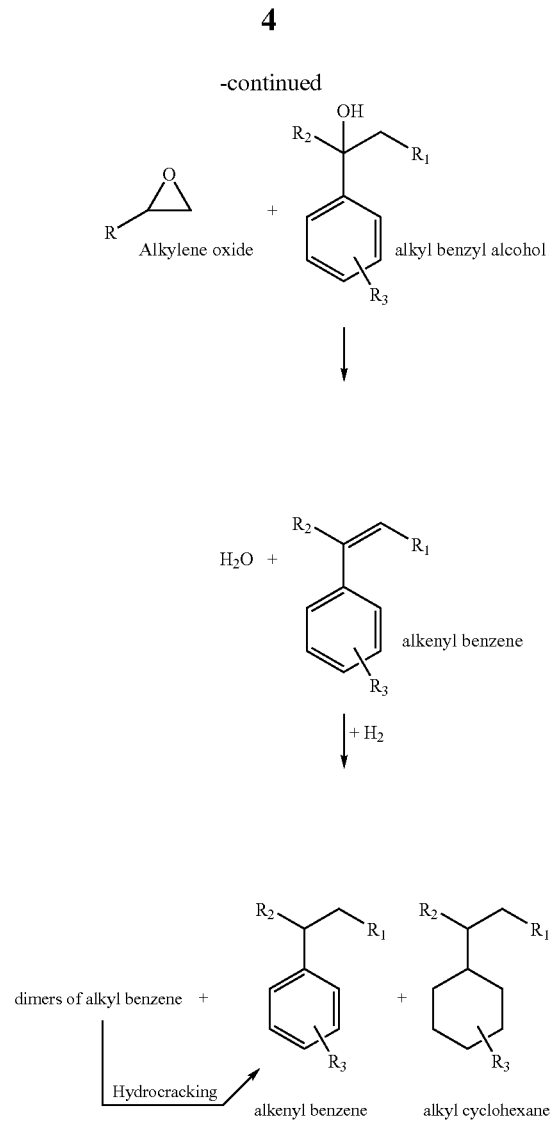

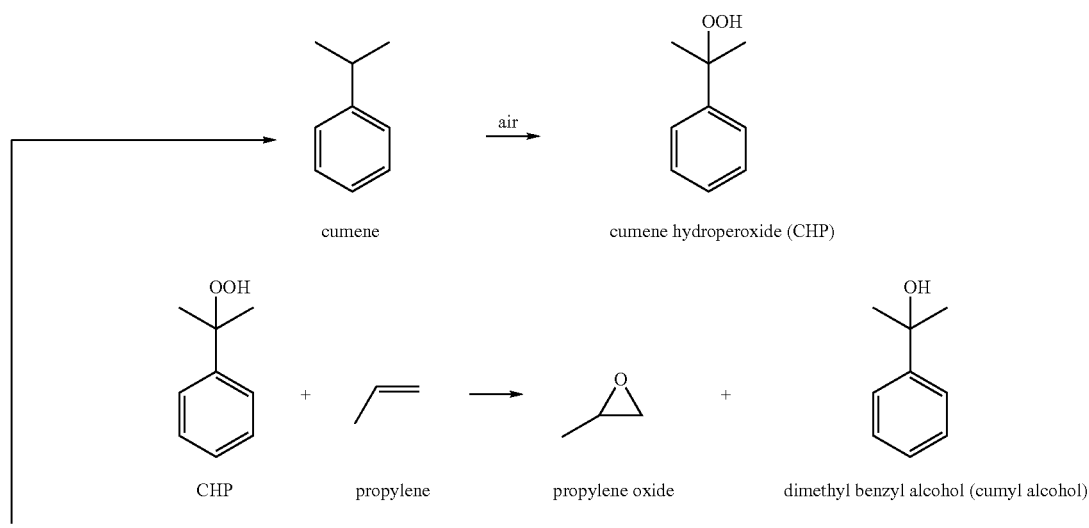

-continued

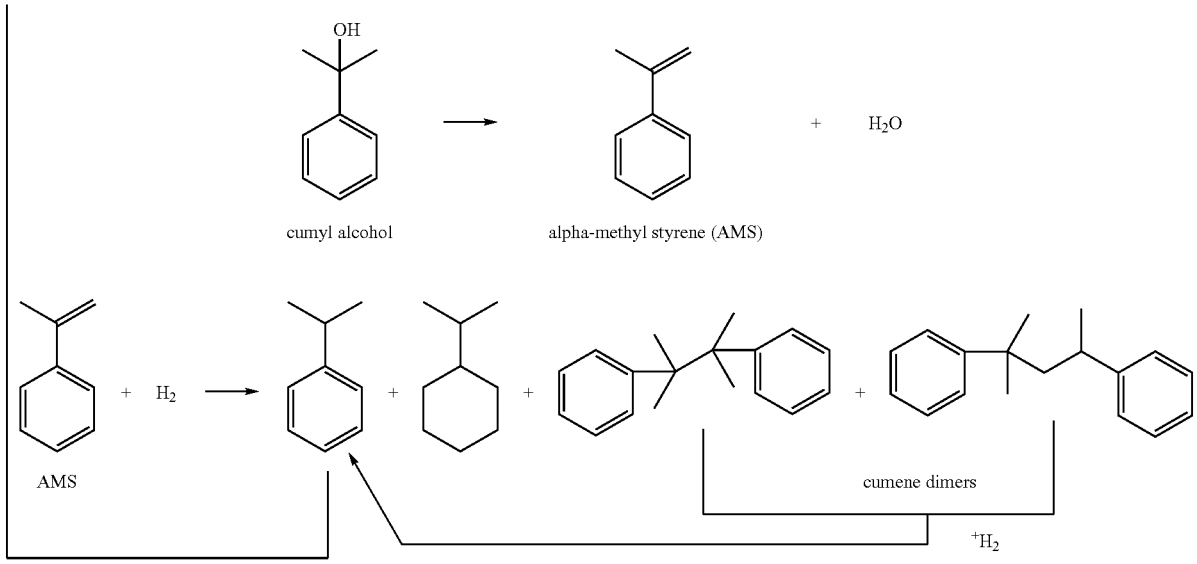

Although ethylbenzene is the alkylbenzene compound most widely used in the preparation of an alkylene oxide compound at present, it has been found that the process step for oxidizing an alkylbenzene may be carried out at higher conversion and higher selectivity if the alkylphenyl compound employed is an alkylbenzene in which the alkyl substituent is a branched alkyl substituent comprising from 3 to 10 carbon atoms. A more preferred alkylphenyl compound contains 1 or 2 alkyl substituents. An alkylphenyl compound containing several substituents, particularly 2 or 3 alkyl substituents, has the advantage that it can contain several hydroperoxide groups. A particular embodiment of the present invention is directed to the reaction in which the alkylphenyl compound is cumene, as illustrated in Pathway II, para, meta, or ortho-di(iso-propyl)benzene or mixtures thereof.

The oxidation of the alkylphenyl may be carried out by any suitable process known in the art. For example, the oxidation may be carried out in the liquid phase in the presence of a diluent. This diluent is preferably a compound which is liquid under the reaction conditions and does not react with the starting materials and product obtained. However, the diluent may also be a compound necessarily present during the reaction. For example, if the alkylphenyl is cumene the diluent can be cumene as well.

The product obtained in the step for oxidizing alkylbenzene may be used as such in the step for epoxidation of olefin, some compounds may be separated off or only part of the product obtained may be used in next step and part may be used in part of a different process.

In the epoxidation of olefin step, alkylphenyl hydroperoxide obtained in the step for making alkylbenzene hydroperoxide is contacted with olefin in the presence of a catalyst to obtain an alkylene oxide and hydroxyalkylbenzene. A catalyst which may suitably be used in such process comprises a Group IVB, VB, or VIB metal, particularly titanium-containing or molybdenum-containing catalyst such as titanium on silica and/or silicate, heterogeneous titanium catalyst or heterogeneous molybdenum catalyst. A particularly suitable catalyst is described in EP-B-345856, which is hereby incorporated by reference. Such catalyst comprises titanium in chemical combination with a solid silica and/or inorganic silicalite which catalyst is obtainable by a) impregnating the silicium compound with a stream of gaseous titanium tetrachloride, b) calcining the obtained reaction product of step a), and c) hydrolyzing the product of step b). The reaction generally proceeds at moderate temperatures and pressures, in particular, at temperatures in the range of from 0° C. to 200° C., preferably in the range of from 25° C. to 200° C. The precise pressure is not critical so long as the reaction mixture is maintained in the liquid state. Atmospheric pressure may be satisfactory. In general, pressures may be in the range of from 1 to $100 \times 10^5$ N/m².

Other non-limiting examples of suitable titanium-containing catalysts include titanium-containing silicon oxide catalysts disclosed in U.S. Pat. No. 6,323,147, ES2,165,771, and WO 01/56693, all of which are herein incorporated by reference, which can be made by mixing a silica source, a titanium source and a quarternary ammonium ion as a template in a solvent to obtain a solid containing a catalyst component and the template, and extracting the obtained solid in a solvent to obtain a catalyst by removing the template, which is optionally subsequently silylated. Another non-limiting example of a suitable epoxidation catalyst is a synthetic zeolite-containing catalyst as described in EP100,119, EP230,949, GB2,071,071, U.S. Pat. No. 4,410,501, U.S. Pat. No. 4,666,692 and U.S. Pat. No. 4,701,428, all of which are herein incorporated by reference. Illustrative examples of organic molybdenum-containing catalysts are described in U.S. Pat. No. 4,772,731, U.S. Pat. No. 5,017,712,U.S. Pat. No. 4,593,012, U.S. Pat. No. 4,590,172, U.S. Pat. No. 4,661,463, U.S. Pat. No. 4,687,868, U.S. Pat. No. 4,607,113, EP58,473, U.S. Pat. No. 3,480,563, U.S. Pat. No. 3,453,218, U.S. Pat. No. 3,434,975, Re30,642, and U.S. Pat. No. 3,351,635, all of which are herein incorporated by reference. An example of a suitable vanadium catalyst includes the catalyst described in U.S. Pat. No. 3,350,422 and that for a tungstun-containing catalyst can be found in U.S. Pat. No. 3,3511,635, both of which are herein incorporated by reference.

The olefin used in the process of the present invention will depend on the alkylene oxide to be prepared. Preferably, the olefin contains from 2 to 10 carbon atoms, more preferably from 2 to 8 carbon atoms. As a particular embodiment of the present invention, the olefin is propene (also known as propylene).

At the conclusion of the epoxidation reaction, the liquid mixture comprising the desired products is separated from the catalyst. The alkylene oxide compound may then be separated from the reaction product in any way known to be suitable to someone skilled in the art. The liquid reaction product may be worked up by fractional distillation, selective extraction and/or filtration. The catalyst, any solvent which might be present and any unreacted olefin or alkylphenyl hydroperoxide may be recycled for further utilization.

The epoxidation process step may be carried out with the catalyst in the form of a slurry, a moving bed or a fluidized bed. However, a fixed bed is preferred for large-scale industrial applications. The process may be carried out in a batch-wise manner, semi-continuously or continuously. The liquid containing the reactants may then be passed through the catalyst bed, so that the effluent from the reaction zone is substantially free from catalyst.

As a particular embodiment of the present invention, part of the product of step (i) is used in the reaction of the alkylphenyl hydroperoxide to obtain a phenolic compound and ketone-containing compound, such as methyl methyl ketone (also known as "acetone") where alkylbenzene is cumene. The phenolic compound obtained may contain substituents. The reaction of the alkylphenyl hydroperoxide may be catalyzed by contacting the alkylphenyl hydroperoxide with an acidic catalyst such as those containing sulfur. The acidic catalyst used may be sulfuric acid, hydrochloric acid, perchloric acid, sulfur dioxide and sulfur trioxide; organic acids such as benzenesulfonic acid, p-toluenesulfonic acid, cresolsulfonic acid and chloroacetic acid; solid acids such as silica-alumina, alumina and acidic ion exchange resins; heteropolyacids such as tungstosilicic acid, tungstophosphoric acid and molybdophosphoric acid. Preferably, sulfuric acid and/or cresolsulfonic acid are used. The amount of catalyst to be used is usually in the range of from 0.0001% wt to 1% wt, based on the reaction mixture to be treated. The reaction temperature is usually in the range of from about 30° C. to about 150° C.

The alkylphenyl hydroperoxide may be subjected to the afore-mentioned reaction to yield phenolic compound(s) after other compounds have been separated off from the reaction product of the step for making alkylbenzene hydroperoxide. However, it is preferred to subject part of the reaction product of the alkylbenzene hydroperoxide formation step directly to the decomposition reaction for making phenolic compound.

The reaction of alkylphenyl hydroperoxide to produce phenolic compound usually produces by-products. By-products which are frequently found are various substituted alkylbenzenes from side reactions, e.g. ethylbenzene and 1-methyl styrene. In order to further increase the yield of the present process, the desired products of phenolic compounds and ketone-containing compound(s) may be separated from the reaction product(s) in the phenolic compound-producing step, after which either all or part of the remaining reaction product is subjected to hydrogenation in the step for converting alkylphenyl alcohol back to alkylbenzene. Therefore, the process according to the present invention preferably comprises separating at least part of the phenolic compound and ketone-containing compound from the reaction product of this step, and contacting either all or part of the remaining reaction product with hydrogen in the step for converting alkylphenyl alcohol to alkylbenzene. Compounds which are obtained in the phenolic alkylphenyl alcohol to alkylbenzene and which are preferably sent to the step for hydrogenating alkylphenyl alcohol are ethylbenzene, 1-methyl styrene, etc. Therefore, any fraction of the reaction product of the phenolic compound-producing step which is sent to the step for hydrogenating alkylphenyl alcohol contains side products of alkylbenzenes used in the process, e.g. ethylbenzene and/or 1-methyl styrene. The reaction product of the phenolic compound-producing step may be sent to the step for hydrogenating alkylphenyl alcohol as such, or the reaction product of the phenolic compound-producing step is combined with the reaction product of the step for making phenolic compound from which alkylene oxide has been separated off, before being sent to the step for hydrogenating alkylphenyl alcohol.

The desired phenolic compound and ketone-containing compound may be separated from the reaction product of the phenolic compound-producing step in any way known to someone skilled in the art. Preferably, the phenol and ketone are substantially removed from the reaction product of the phenolic compound-producing step, while at least part of the reaction products other than phenolic compound and ketone-containing compound is sent back to the integrated process.

As a particular embodiment of the present invention, if part of the alkylphenyl hydroperoxide is converted into phenolic compound and ketone-containing compound, the alkylphenyl compound may be cumene, as this gives phenol and acetone in the phenolic compound-producing step.

Subsequently, at least part of the reaction product containing hydroxyalkylphenyl, from which an alkylene oxide compound has been separated off, is subjected to hydrogenation. The hydrogenation treatment is carried out in the presence of a hydrogenation catalyst.

As a preferred non-limiting embodiment, the step of converting alkylphenyl alcohol in the residual product stream to alkylbenzene is carried out via a catalytic distillation reaction. The process involves feeding alkylphenyl alcohol-containing feed stream to a catalytic distillation reactor into a feed zone, contacting the alkylphenyl alcohol-containing feed stream with a fixed bed catalytic packing to concurrently carry out a one-step dehydration-hydrogenation reaction, while fractionating and removing the lower boiling point alkylbenzene produced in the catalytic distillation zone by distillation before it is converted to alkylcyclohexane or dimers of alkylphenyl alcohol, while unconverted alkylphenyl alcohol or di-alkylphenyl alcohol continues refluxing in the catalytic distillation zone until being converted to alkylbenzene. A heating device with heating media may be utilized to provide the heat needed for the distillation reaction.

The catalytic distillation operation mode provides the advantage of enhancing the selectivity of the reaction to alkylbenzene, such as cumene, by continuously removing the product alkylbenzene via fractional distillation in the catalytic distillation reactor. The continuous catalytic distillation operations with concurrent catalytic reaction and fractionation of product benefit from the fact that the boiling points of the majority of alkylphenyl alcohols are higher than those for the corresponding product alkylbenzenes. The present inventive embodiment of dehydration/hydrogenation in a catalytic distillation mode provides further advantages by lowering the required capital expenditure through operating multiple dehydration and catalytic hydrogenolysis reactions as well as fractionation steps in a single reactor without a separate hydrogenation reactor with its accompanying heat exchange equipment and controls. The combination of catalytic distillation and the particular catalytic hydrogenation reaction results in a better selectivity toward the saturation of the alkenyl chain produced from the dehydration of the alkylphenyl alcohol, without hydrogenation of the aromatic bonds.

As a specific embodiment of the present invention, the olefin is propene, the alkylene oxide produced is propylene oxide, the alkylbenzene is cumene (also known as i-propylbenzene) and the alkylphenyl alcohol is cumyl alcohol (also known as 2-phenyl-2-propanol) as illustrated in Pathway II. Table 1 below shows that cumene has a significantly lower boiling point than both cumyl alcohol and cumene dimers, which are 2,3-dimethyl-2,3-diphenylbutane and 2-methyl-2,4-diphenylpentane, etc. Therefore, in the catalytic distillation operation, cumene is recovered from the overhead or side-draw above the catalyst bed upper from the catalytic distillation zone, leaving unconverted cumyl alcohol in the catalyst bed for further reaction. Any cumene dimers, having the highest boiling points, stay in the bottom section of the reactor, and will not be distilled out of the top of the reactor. The mixture at the bottom of the reactor, which may contain cumene dimers, may be withdrawn as a bottom stream.

TABLE 1

| Compound | Boiling Point at 1 Atm. Pressure, ° C. |
|---|---|
| cumyl alcohol | 201 |
| cumene | 152–154 |
| alpha-methylstyrene | 165–169 |
| iso-propylcyclohexane | 155 |
| 2-methyl-2,4-diphenylpentane | 300–320 |
| 2,3-dimethyl-2,3-diphenylbutane | 300–320 |

The alkylphenyl alcohol may also be ethylphenyl alcohol (also known as 1-hydroxyl-1-phenyl ethane or hydroxyethylbenzene) wherein the alkylbenzene produced is ethyl benzene. In still another specific embodiment of the present invention, the alkylphenyl alcohol is ortho, meta, or para-di-(2-hydroxyl-2-propyl)benzene, 4-(2-hydroxy-2-propyl) cumene, 3-(2-hydroxy-2-propyl)cumene, 2-(2-hydroxy-2-propyl) cumene, or mixtures thereof, and the alkylbenzene is meta, ortho, or para-di-(isopropyl) benzene, or mixtures thereof. In a particular embodiment, the alkylphenyl alcohol is para-di-(2-hydroxyl-2-propyl)benzene and the alkylbenzene is para-di-(isopropyl) benzene.

As a particular embodiment of the present invention, less than about 1.0%, particularly less than about 0.5%, and more particularly less than about 0.2% by weight of the alkylbenzene produced is converted to alkyl cyclohexane ($R_1 CH_2R_2CH$(cyclohexane)), and less than about 0.1%, particularly less than about 0.05%, and more particularly less than 0.01% by weight of the alkylbenzene produced is converted to side products in the form of dimer(s) or polymer(s) of alkylbenzene.

As a particular embodiment, any heavy dimers or polymers of alkylbenzenes, such as cumene dimers, made in the catalytic distillation mode having higher boiling points than alkylbenzenes and alkylphenyl alcohols, fall to the bottom of the catalytic distillation reactor. The dimers or oligomers in the bottom of the reactor may be withdrawn as a part of the bottom stream and may optionally be fractionated to recover alkylbenzene, alkylphenyl alcohol and alkenylbenzene for recycle back to the catalytic distillation column; and the stream richer in dimers or oligomers may subsequently be hydrogenated, e.g., in a fixed bed mode, to produce more alkylbenzenes, such as cumene. Optionally, the dimers or oligomers can be hydrogenated/hydrocracked at the bottom of the reactor. Non-limiting illustrative examples of side product dimers made from dimerization of cumene include 2,3-dimethy-2,3-diphenyl butane and 2-methyl-2,4-diphenylpentane as shown in Pathway II. Illustrative and non-limiting examples of suitable hydrocracking catalysts for converting dimers of alkylbenzenes to alkylbenzene, such as converting 2,3-dimethyl-2,3-diphenyl butane and 2-methyl-2,4-diphenylpentane to cumene include catalysts comprising Group VIII metal or Group IB metal on a support, particularly those comprising copper, palladium, platinum and nickel on a support. Non-limiting illustrative examples of a support include silica, silica-alumina, and zeolite, such as Mordenite, Na/H-Mordenite, H-Mordenite, beta-zeolite, H-beta-zeolite, Y-zeolite, H-Y-zeolite, and the like. In one particular embodiment of the present invention, the catalysts contain from about 0.1% wt to about 5% wt, particularly from about 0.2% wt to 2% wt, calculated as the weight of the metal on the basis of the total weight of the catalyst, of Group VIII metal or a Group VIII metal compound as principal catalytic component, alone or with promoters and modifiers such as palladium/gold, palladium/silver, cobalt/zirconium, nickel, preferably deposited on an acidic support, which is preferably in acidic hydrogen form. The term "acidic hydrogen form" means 50% or more of ion exchangeable cations are hydrogen (+) ions (also known as "$H^+$" or "proton"). The Group IB metal-containing catalysts preferably contain from about 10% to about 80%, particularly from about 30% to about 70%, more particularly from about 50% to about 60%, as the weight of the oxide basis the total weight of the catalyst, of a Group IB metal, particularly on an acidic support, more particularly on a support in acidic hydrogen form. Specific non-limiting examples of such catalysts include catalysts comprising copper, Raney copper, copper/chromium, copper/zinc, copper/zinc/chromium, copper/zinc/zirconium, copper/silica, copper/zinc/aluminum copper/alumina, copper chromite, palladium/carbon, palladium/H-Mordenite, palladium/alumina, palladium/silica, palladium/silica-alumina and other copper-based catalyst systems. From about 86.0% to about 100.0%, particularly from about 90.0% to about 100.0%, more particularly from about 94.0% to about 100.0%, still more particularly from about 97.5% to about 100.0%, and still more particularly from about 98.0% to about 100.0% by weight of dimers of alkylbenzenes is converted to alkylbenzene at a temperature from about 140° C. to about 300° C., particularly from about 185° C. to about 235° C., and more particularly from about 185° C. to about 225° C.

As a non-limiting illustrative example, the catalytic distillation bed (also known as catalytic distillation zone) is positioned centrally in the catalytic distillation reactor at a point below the top (where alkylbenzene is recovered as an overhead) or side draw of alkylbenzene product stream, while the feed stream and the hydrogen-containing stream is fed into the reactor below the catalytic distillation bed. This configuration allows the feed stream and hydrogen to move up into the bed and contact the catalyst under the conditions described herein to hydrogenate the side chain. In the alternative, the feed stream may be fed into the catalytic distillation reactor from above the catalytic distillation bed and move down into the catalytic distillation bed and contact the hydrogen fed from below the catalytic distillation bed; or the feed stream may also be fed into the catalytic bed. Optionally, the entry point of the feed stream into the reactor may be adjusted according to the concentration of the feed stream, e.g. the higher the concentration of the alkylphenyl alcohol in the feed stream, the higher up will be the entry point for the feed stream. A non-limiting illustrative example of a suitable catalytic distillation reactor has an outer diameter from about 0.01 meter to about 20 meters, and particularly from about 0.5 meter to about 10 meters; and a height from about 0.2 meter to about 200 meters, and particularly from about 1 meter to about 100 meters.

The catalyst packing is of such a nature as to allow vapor to flow through the catalytic distillation bed, while providing a sufficient surface area for catalytic contact, and effectively fractionating the reaction products. As a non-limiting illustrative example, the catalysts may be filled/loaded into a plurality of trays/baffles/packings, and the like, designed to provide sufficient fractionation mechanism, and maintained in a flooded state as the liquid in the reactor passes down through the trays/baffles/packing to the lower trays/packings/baffles in the catalytic distillation zone. The material may then be fractionated on the lower tray as in a conventional fractionation tower. Optionally, additional trays/packings without catalyst may be employed below the catalytic distillation bed to improve separation among the reactants and products, especially between alkylphenyl alcohol and alkylbenzene dimer(s)/oligomers thus reducing alkylphenyl alcohol content in the bottom of the reactor. The hydrogen and the residual product stream as feed stream to the reactor may enter either above or below these non-catalytic trays. The feed stream to the catalytic distillation reactor containing higher boiling reactant alkylphenyl alcohols, such as cumyl alcohol, is continually contacted with the catalyst loaded in the catalyst bed in a catalytic distillation reaction zone, and concurrently fractionating the resulting reaction mixture in the fixed catalyst bed; the lower boiling product alkylbenzenes, such as cumene, pass upward through the catalyst beds and are recovered as a part (usually the majority) of the overhead or side draw above the catalyst bed. The hydrogenation reaction (coupled with dehydration) and fractionation occur concurrently over the fixed catalyst bed, which serves as both catalyst and distillation packing in the catalytic distillation reactor. The unreacted alkylphenyl alcohols and alkenylbenzenes left behind in the catalyst bed are in contact with the catalyst for conversion into alkylbenzene. Most of the alkylphenyl alcohols are dehydrated to form alkenylbenzenes which only exist in transient, and are immediately hydrogenated to alkylbenzenes in the catalyst bed. Optionally, additional packings/trays are employed above the catalytic distillation zone to provide reflux of alkylbenzene. The overhead or side draw, comprising a high concentration of alkylbenzene, above the catalyst bed may be recycled back for reuse via a wet oxidation step for making alkylbenzene hydroperoxide without a dewatering step. The same alkylbenzene-rich stream may be subject to a hydrogen and/or water separation step to recover hydrogen and/or remove the dense water and optionally dried with drying agent such as molecular sieves, and then returned to the catalytic distillation reactor above the catalyst bed for further reflux/purification. The alkylbenzene recovered may be of a high enough purity to be sold as is on the market or recycled for reuse in making alkylbenzene hydroperoxide. The overhead or side draw, optionally having water and hydrogen removed, comprises from about 90% to about 100%, particularly from about 98% to about 100% and more particularly from about 99.5% to about 100 percent by weight of alkylbenzene; from about 0% to about 10%, particularly from about 0% to about 5%, and more particularly from about 0% to about 1% percent by weight of alkylphenyl alcohol, less than about 1% particularly less than about 5%, more particularly less than about 0.1 percentage by weight of alkenylbenzenes; less than about 5%, particularly less than about 1%, and more particularly less than about 0.1 percent by weight of dimers or oligomers of alkylbenzene; less than about 5%, particularly less than about 1%, and more particularly less than about 0.2 percent by weight of alkylcyclohexane.

Where a feed stream comprising cumyl alcohols is fed to the present catalytic distillation reactor, the overhead or side draw above the catalyst bed, after the removal of water and/or hydrogen, comprises from about 90% to about 100%, particularly from about 98% to about 100% and more particularly from about 99.5% to about 100% percent by weight of cumene; from about 0% to about 10%, particularly from about 0% to about 5%, and more particularly from about 0% to about 1% percent by weight of cumyl alcohol, less than about 5%, particularly less than about 1%, more particularly less than about 0.1 percentage by weight of alpha-methyl styrene; less than about 5%, particularly less than about 1%, and more particularly less than about 0.1 percent by weight of dimers or oligomers of cumene; less than about 5%, particularly less than about 1%, and more particularly less than about 0.2 percent by weight of isopropylcyclohexane.

Without limiting the scope of the present invention, it is proposed that the mechanism that produces the effectiveness of the present process is the condensation of a portion of the alkyphenyl alcohol or alkenylbenzene-containing vapors in the reaction system, which occludes sufficient hydrogen in the condensed liquid to obtain the requisite intimate contact between the hydrogen and the alkenylbenzene, such as alpha-methyl styrene, in the presence of the catalyst to result in the hydrogenation of the side chains of alkenylbenzene.

As a particular embodiment, a reflux condenser is included in the system. The reflux ratio can vary over the rate of 1 to 20:1. In practice, the higher ratio may be used to compensate for a short catalyst bed. In commercial size units, a long catalyst bed is normally provided, and lower reflux ratios and hence higher unit productivity is usually obtained.

The temperature in the catalytic distillation reactor is determined by the boiling point of the alkyl benzene at any given pressure. The distillation reactor is operated at a pressure such that the reaction mixture is boiling in the bed of catalyst. Generally, pressure in the range of 0 psig to 400 psig may be employed, particularly from about 0 psig to about 140 psig (or about 1–10 bars).

For the conversion of a cumyl alcohol-containing feed stream, the pressure can be from about 0 psig to about 400 psig, particularly from about 5 psig to about 300 psig, and more particularly from about 0 psig to about 140 psig (or about 1–10 bar). It is understood that cumene boils at about 152–154° C. at about 0 psig (1 bar), and at higher pressure, the boiling point of cumene will rise. As an illustrative non-limiting example, the present process operates at overhead pressure below 50 psig. Preferably, the reactor is operated at low pressure to reduce the temperature to prevent unwanted polymerization and so that higher selectivity can be achieved. At about 0 psig (atmospheric pressure), the temperature at the bottom of the reactor is higher than about 200° C., and close to about 155° C. at the top, and about 150 to 210° C. in the catalytic distillation zone. The feed weight hourly space velocity (WHSV) may vary over a very wide range within the other condition parameters, and may be from about 0.1 to about 10, particularly from about 0.2 to about 2 liters per hour. WHSV, as used herein, means the unit weight of feed per hour entering the reaction distillation reactor per unit weight of catalyst in the reactor.

As an illustrative example, the residual product stream fed to the catalytic distillation or fixed bed reactor for hydrogenation contains from about 1% to about 100%, particularly from about 5% to about 75%, and more particularly from about 10% to about 40% by weight of alkylphenyl alcohol; from about 0% to about 99, particularly from about 25% to about 95%, and more particularly from about 60% to about 90% by weight of alkylbenzene; from about 0% to about 20%, particularly from about 0% to about 5%, and more particularly from about 0% to about 1% by weight of alkenylbenzene; and from about 0% to about 25%, particularly from about 0% to about 10%, and more particularly from about 0% to about 5% by weight of alkylbenzene hydroperoxide. As specific illustrative example of a particular embodiment of the present invention, the residual product stream, fed to the hydrogenation reactor contains from about 1% to about 100%, particularly from about 5% to about 75%, and more particularly from about 10% to about 40% by weight of cumyl alcohol; from about 0% to about 99%, particularly from about 25% to about 95%, and more particularly from about 60% to about 90% by weight of cumene; from about 0% to about 20%, particularly from about 0% to about 5%, and more particularly from about 0% to about 1% by weight of alpha-methyl styrene; from about 0% to about 5 weight percent of ethyl benzene; from about 0% to about 5 weight percent of di-, tri-isopropyl benzene, ethyl benzene, propyl-benzene, ethyl-isopropyl benzene, etc., or mixtures thereof; and from about 0% to about 25%, particularly from about 0% to about 10%, and more particularly from about 0% to about 5% by weight of cumene peroxide.

Where a feed stream to the catalytic distillation reactor, such as a residual product stream, comprises a di-isopropyl benzene (DIPB), it may contain a small amount, e.g. less than 5% by weight, of cumene, tri-isopropyl benzene, ethyl benzene, propyl-benzene, ethyl-isopropyl benzene, etc., or mixtures thereof. The streams which are cycled to peroxide, epoxidation, hydrogenation reactors have similar properties due to side reactions. It has been found that compounds containing ortho-substituted alkylphenyls are less preferred for use in the process according to the present invention, as they are generally less reactive. Preferably, at least 80% wt of the alkylbenzenes for use in step (i) of the process of the present invention are meta-substituted or para-substituted alkylphenyls. More preferably, at least 90% wt, more specifically at least 95% wt, of the alkylphenyls for use in the process of the present invention are meta-substituted or para-substituted alkylbenzenes.

In order to prevent build-up of less reactive alkylbenzenes in the process according to the present invention, it is especially preferred that the process comprises a further step by which at least part of the less reactive alkylbenzene compounds are removed. Preferably, such process step comprises subjecting at least part of the product of step (i) to distillation. The bottom product may be used in step (ii). The product distilled off will contain a relatively large amount of less reactive alkylaryls. This product may be sent to a transalkylation unit as described above. In the transalkylation unit, the product may be converted into a product containing more reactive compounds or it may be converted into compounds containing a single alkyl substituent on the aromatic group.

The hydrogenation rate must be adjusted such that it is sufficient to support the hydrogenation reaction and replace hydrogen lost from the catalyst. At least a stoichiometric amount of hydrogen relative to the alkenylbenzene (produced in transient before converted to alkylbenzene) must be present in the system to be available for the reaction. As a non-limiting example, a small excess of hydrogen flow is provided to occlude the hydrogen into the liquid and to accommodate the nature of this reaction between a gas and a liquid.

Hydrogenation carried out in a reactor for catalytic distillation requires only a fraction of the hydrogen partial pressure required in prior art liquid phase processes for this type of stream, but gives the same or better result. Thus, the capital investment and operating expense for the present hydrogenation process is substantially lower than prior art processes. The lower hydrogen partial pressures allow for the use of the more active catalyst at the lower temperatures without unduly hydrogenating the aromatic part of the product.

The present catalytic distillation reaction also benefits from having the reaction occurring concurrently with distillation, therefore, the initial reaction products and other stream components are removed from the reaction zone as quickly as possible, reducing the likelihood of side reaction(s). Moreover, because all the components are boiling, the temperature of reaction is controlled by the boiling point of the mixture at the system pressure. The heat of reaction simply creates more boil-up but no increase in temperature at a given pressure. As a result, a great deal of control over the rate of reaction and distribution of products may be achieved by regulating the system pressure. Also, adjusting the throughput gives further control of product distribution and, to a degree, control of the side reactions such as aromatic ring hydrogenation, dimerization and oligomerization. A further benefit that this reaction may gain from catalytic distillation is the washing effect that the internal reflux provides to the catalyst, thereby reducing polymer build up and coking of the catalyst. Internal reflux may vary over the range of 0.2–20 L/D (wt. liquid just below the catalyst bed/wt./distillate).

The catalytic material employed in the hydrogenation process functions as both a catalyst and a distillation packing. The particulate catalyst material may be in any form, structure or size which provides sufficient surface area to allow a reasonable reaction rate. It may be a powder, small irregular chunks or fragments, small beads and the like and compositions thereof. Non-limiting examples of the structure of the catalytic distillation beds include disposing particulate catalyst material within a porous plate or screen to contain the catalyst and provide distillation surfaces in the form of a wire mesh structure, such as a wire mesh tubular structure or any other similar structure. It may also be a flexible, semi-rigid open mesh tubular material, such as stainless steel wire mesh, filled with a particulate catalytic material. Specific examples of the catalyst structure can be found in U.S. Pat. Nos. 5,266,546, 4,242,530, 4,443,559, and 5,348,710, which are incorporated herein by reference.

Any suitable hydrogenation catalyst may be used. As an illustrative embodiment of the present invention, the hydrogenation catalyst comprises a metal on a solid carrier which metal catalyses hydrogenation. In one particular embodiment of the present invention, the catalyst comprises from about 0.1% to about 5% wt, particularly from about 0.2% to 2% wt, of Group VIII metal or a Group VIII metal compound as principal catalytic component, alone or with promoters and modifiers such as palladium/gold, palladium/silver, cobalt/zirconium, nickel, preferably deposited on a support such as zeolite, other molecular sieves, alumina, fire brick, pumice, carbon, silica, silica-alumina, thermally stable resin or the like. One illustrative example of a suitable catalytic material comprises palladium oxide or palladium, preferably 0.1% to 5.0% wt, supported on an appropriate support medium such as alumina, carbon, zeolite (such as Mordenite or H-Mordenite) or silica. The gamma alumina supported copper based catalyst disclosed in U.S. Pat. No. 4,822,936, which is hereby incorporated by reference, may also be used.

As other particular embodiments of the present invention, Group IB metals of the Periodic Table of Elements, such as copper, may be used as the principle catalytic component, alone or with promoters and modifiers such as chromium, zinc, zirconium, aluminum, magnesium, a rare earth metal, Group VIII metals, etc., particularly those supported on a carrier, for hydrogenation. The Group IB metal-containing catalysts preferably contain from about 10% to about 80%, particularly from about 30% to about 70%, more particularly from about 50% to about 60%, as the weight of the oxide basis the total weight of the catalyst, of a Group IB metal, particularly on a support. Some specific illustrative examples include commercially available copper on silica catalyst, T-366 (having approximately 54 wt. % of copper on silica as a press extrudate or formed extrudate), obtainable from Sud Chemie; copper chromite catalyst, G-22/2, obtainable from Sud Chemie; and Cu/Zn/Zr catalyst prepared according to Example 3 of U.S. Pat. No. 5,475,159, which is hereby incorporated by reference; and the like. Combinations of these catalysts may also be used. Such catalysts were found to give good results at relatively low temperature. In one non-limiting illustrative embodiment of the present invention, in the step of converting alkylphenyl alcohol to alkylbenzene, these catalysts are preferably used at a temperature of from 100° C. to 250° C. Such catalysts may comprise from about 5 percent by weight to about 80 percent by weight, calculated as the oxide, basis the total weight of the catalyst, of copper. Further, such catalysts preferably contain from about 10 percent by weight to about 80 percent by weight, calculated as the oxide, basis the total weight of the catalyst, of zinc. A particular example of the catalyst contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, and from about 0.1 percent by weight to about 20 percent by weight, calculated as the oxide, basis the total weight of the catalyst, of rare earth. A further preferred catalyst contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, and from about 0.05 percent by weight to about 30 percent by weight, basis the total weight of the catalyst, of aluminum. A further preferred catalyst contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, and from about 0.05 percent by weight to about 30 percent by weight, basis the total weight of the catalyst, of zirconium. Another preferred catalyst contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, from about 0.05 percent by weight to about 30 percent by weight, basis the total weight of the catalyst, of zirconium, and from about 0.05 percent by weight to about 30 percent by weight, basis the total weight of the catalyst, of aluminum. And a further preferred catalyst contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, from about 0.05 percent by weight to about 30 percent by weight, basis the total weight of the catalyst, of magnesium, and from about 0.1 percent by weight to about 20 percent by weight, calculated as the oxide, basis the total weight of the catalyst, of rare earth.

The catalyst in the catalytic distillation zone can be reduced, prepared and pre-activated by the following non-limiting illustrative procedure. A catalyst is crushed and sized into appropriate size, e.g. 6–20 mesh, particles. The catalyst is slowly reduced by heating the catalyst particles to a temperature of e.g. about 150–180° C. at a rate of from about 1° C. to about 10° C., particularly from about 1.5° C. to about 5° C. per minute, while flowing about 0.001% to about 0.1%, specifically about 0.02% to 0.10 wt. % hydrogen in nitrogen at a rate of 1–200, specifically 2–30 L/Hr. The catalyst is allowed to reduce at 150–180° C. for 1–10 hours and then the hydrogen content in the nitrogen is doubled every 1–5 hours until the gas is 1–10, specifically 2–5 wt. % hydrogen in nitrogen. The catalyst is reduced for a final one to five hour period and then cooled while maintaining gas flow. After cooling, the reactor is capped without allowing any air to enter and the gas flow is stopped. The reactor is opened in a nitrogen filled environment and the catalyst and silicon carbide are separated by screen sieve.

The 6–20 mesh particles of reduced catalyst, prepared by the afore-mentioned procedure are loaded onto bed supports made of porous plate or screen in a distillation reactor in a nitrogen filled environment. Glass wool can also be used to support the catalyst particles. Hydrogen gas is added via a regulator to the apparatus to maintain a pressure between 0–450 psig, (typically between 0–150 psig). The flow rate is adjusted to maintain twice the amount of hydrogen required for the reaction stoichiometry. A feed stream containing alkylphenyl alcohol, such as a stream containing (e.g.10–40 weight %) of 2-phenyl-2-propanol (cumyl alcohol), is fed into the distillation reactor from below the catalyst beds. The bottom section of the distillation reactor is lowered into a heater and then the temperature is raised until the liquid refluxes in the distillation reaction zone containing the catalyst. Lower boiling alkylbenzene, such as cumene, and water are distilled out from the top of the column. Additional alkylphenyl alcohol, such as a cumyl alcohol-containing stream, is continually added with a slight molar excess of hydrogen to replace the amount of alkylphenyl alcohol, such as cumyl alcohol, that is converted to alkylbenzene, such as cumene, and distilled off. The alkyl benzene product, such as cumene, easily separates from the denser water phase. It is optionally dried further with molecular sieves or other suitable drying agents. The alkylbenzene, such as cumene, produced has a purity of more than 98 wt. %, preferably more than 99 wt. %. No measurable alkylphenyl alcohol, such as cumyl alcohol (<0.01 wt. %) is found in the alkylbenzene, such as cumene product. When desired, the bottoms can be removed, optionally diluted with cumene and sent to a fixed bed hydrogenation reactor to make additional alkyl benzene, such as cumene.

As one non-limiting particular embodiment, a hydrogenation treatment in a fixed bed mode without concurrent distillation, i.e. not in a catalytic distillation mode can be used which comprises contacting reaction product with hydrogen at a temperature of from 100° C. to 330° C., preferably of from 140° C. to 300° C., preferably of from 160° C. to 2800° C., preferably of from 180° C. to 260° C., and a pressure of from 0.1 to 100×10⁵ N/m², more preferably of from 0.1 to 50×10⁵ N/m², most preferably of from 0.1 to 30×10⁵ N/m². The ratio (mol/mol) of hydrogen to alkylphenyl alcohol contacted with the catalyst is preferably at least 0.5, more preferably at least 1.0, most preferably at least 1.4.

After hydrogenation, the hydrogenated product comprising alkylbenzene, such as cumene or di-isopropylbenzene, may be recycled for reuse in totality or in part. If only part of the hydrogenated product is recycled, the desired fraction may be separated off in any way known to be suitable to someone skilled in the art.

The invention will be illustrated by the following illustrative embodiments which are provided for illustrative purposes only and are not intended to limit the scope of the instant invention.

ILLUSTRATIVE EMBODIMENTS

Illustrative Embodiment I—Production of Alkylene Oxide and Cumyl Alcohol IA.

The epoxidation catalyst was a catalyst containing titanium on silica which was prepared as described in the Example according to the teaching of EP-A-345856.

The hydrogenation catalyst was a catalyst containing copper, zinc and zirconium prepared according to Example 3 of U.S. Pat. No. 5,475,159.

Fresh cumene and recycled cumene are fed to a reactor. During 8 hours, air was bubbled in at the bottom of the reactor, leaving at the top of the reactor. The reactor was cooled during the reaction. The reaction product obtained contained 28% wt of cumene hydroperoxide, 70% wt of cumene and 2% wt of further compounds.

A reaction mixture containing about 6 mol of 1-octene per mol of cumene hydroperoxide was fed to a reactor containing the fresh epoxidation catalyst described above at a temperature of 40° C. Octene oxide was separated off. It was found that 55% wt of 1-octene was converted into octene oxide.

IB.

Fresh ethylbenzene and recycled ethylbenzene were fed to a reactor. For 8 hours, air was bubbled in at the bottom of the reactor, leaving at the top of the reactor. The reactor was cooled during the reaction due to the exothermic nature of the oxidation. The reaction product obtained contained 10% wt of ethyl benzene hydroperoxide, 88% wt of ethylbenzene and 2% wt of further compounds.

A reaction mixture containing about 6 mol of 1-octene per mol of ethylbenzene hydroperoxide was fed to a reactor containing the fresh epoxidation catalyst described in Example 1 at a temperature of 40° C. Octene oxide was separated off. It was found that 41% wt of 1-octene was converted into octene oxide.

II. Illustrative Embodiment II—Catalytic Distillation of Cumyl Alcohol to Cumene IIA. Preparation of Hydrogenation Catalyst IIA(i). Preparation of Hydrogenation Catalyst T-366 Catalyst A commercially available copper on silica catalyst, T-366, available from Sud Chemie was further processed using the following procedure for the catalytic distillation mode experiments.

Five grams of Sud Chemie T-366 copper on silica catalyst (3 mm tablets) was crushed and sized into 6–20 mesh particles. The catalyst was mixed with 45 grams of 80 mesh silicon carbide and centered inside a 69 cm long stainless steel reactor tube between beds of 20 mesh SiC and glass wool. The reactor tube had an internal diameter of 1.5 cm. The catalyst was slowly reduced by heating the catalyst particles at a rate of 3° C. per minute from 20° C. to 180° C. while flowing 0.05 wt. % hydrogen in nitrogen at a rate of 10 L/Hr. The catalyst was allowed to reduce at 180° C. for 2 hours and then the hydrogen content in the nitrogen was doubled every 2 hours until the gas was 3.2 wt. % hydrogen in nitrogen. The catalyst was reduced for a final two-hour period and then cooled while maintaining gas flow. After cooling, the reactor was capped without allowing any air to enter and the gas flow was stopped. The reactor was opened in a nitrogen filled glove box and the catalyst and silicon carbide were separated by screen sieve.

II(A)(ii). Preparation of Hydrogentation Catalyst Pd-Mordenite Catalyst

A mixture of 1500 grams of sodium mordenite, (having the following properties: a surface area of 430 square meters per gram; an average crystallite size of around 1 micron; a cyclohexane adsorption uptake of 7.6 cc/g; and a molar silica to alumina ratio of 11.1), 9000 grams of ammonium nitrate and 15 liters of 1.5 M nitric acid was heated to 50° C. and stirred for five hours. The solid material was filtered off and washed with 25 liters of deionized water. This treatment of the Mordenite with ammonium nitrate in nitric acid was repeated twice with fresh ammonium nitrate and nitric acid each time. After each treatment the solid material was filtered off and washed with water and dried overnight at 120° C. Palladium was added to the zeolite to a level of 0.35 percent by weight by treatment with an aqueous solution containing Tetraamine palladium nitrate and an excess of ammonium nitrate prepared by dissolving 6.55 grams of tetraamine palladium nitrate in 308 grams of deionized water and adding to this solution 4.92 grams of ammonium nitrate. The palladium solution was then co-mulled with 1083 grams of dealuminated mordenite having an LOI (loss on iginition at 750° C. for 2 hours) of 10.6%. The palladium-containing mordenite was uniformly mixed and then 338 grams of pseudoboehmite alumina (Catapal B which is commercially available from Vista Chemical Company) having an LOI of 28.4% was added and allowed to mix. The mixture was extruded and the 1.6 mm extrudates were dried in air for 16 hours at 125° C., and then calcined in flowing air at 500° C. for two hours. The catalyst was crushed and sized to 6–20 mesh particles and then further hydrogenated using the procedure as described in IIA (i) above for the catalytic distillation mode experiments.

II(B). Catalytic Distillation

II(B)(i). Using T-366 Catalyst

The 6–20 mesh particles of reduced T-366 catalyst, prepared by the procedure of Illustrative Embodiment II(A)(i), were loaded into the reflux zone of a thick walled 31 cm long Vigreux column with an internal diameter of 1.5 cm while inside a nitrogen filled glove box. A small piece of glass wool was used to support the catalyst particles. The column was attached to a thick walled 250 ml round bottom flask which served as the bottom segment of the reactor for catalytic distillation. Hydrogen gas was added via a regulator to the apparatus to maintain a pressure between 1 and 10 bar. The flow rate was adjusted to maintain twice the amount of hydrogen required for the reaction stoichiometry. 50 grams of 2-phenyl-2-propanol (cumyl alcohol) from Avacado Chemical was added to the 250 mL flask which contained a magnetic stir bar at the bottom of the round bottom flask. The flask containing the cumyl alcohol was lowered into a heater and then the temperature was raised until the liquid refluxed in the Vigreux column containing the catalyst. Lower boiling cumene and water were distilled out from the top of the column. Additional cumyl alcohol was continually added with a slight molar excess of hydrogen to replace the amount of cumyl alcohol that was converted to cumene and distilled off. The cumene product easily separated from the denser water phase. It was optionally dried further with 3 Å molecular sieves. The results are provided in TABLE 2 below. As shown, the top product stream produced, (after removal of the water), had a purity of cumene of >99.5 wt. %. No measurable cumyl alcohol (<0.1 wt. %) was found in the cumene product. When desired, the bottoms can be removed, optionally diluted with cumene and sent to a fixed bed hydrogenation reactor to make additional cumene.

TABLE 2

Results of Catalytic Distillation of Cumyl Alcohol to Produce Cumene - T-366 Catalyst

| Component | Feed | Top Product* |
|---|---|---|
| 2-Phenyl-2-propanol, (wt %) | 99.2 | <0.1 |
| α-Methyl styrene, (wt %) | 0.4 | 0.2 |
| Cumene, (wt %) | 0.1 | >99.5 |
| Isopropylcyclohexane, (wt %) | 0.1 | 0.1 |
| Other, (wt %) e.g. cumene hydroperoxide | 0.2 | 0.1 |
| Cumene dimer | <0.1 | Not detected |

*after removing the water produced

II(B)(ii). Catalytic Distillation Using Pd-Mordenite Catalyst

The reduced Pd-Mordenite catalyst, prepared by the procedure of Illustrative Embodiment II(A)(ii) above, were loaded into the reflux zone of a thick walled 31 cm long Vigreux column with an internal diameter of 1.5 cm while inside a nitrogen filled glove box. The same procedures described in II(A) (i) and II(A) (ii) above were followed for the set-up and operation of a catalytic distillation operation. The results are provided in TABLE 3 below. As shown, the top product stream produced, after removal of water, had a purity of cumene of >99.6 wt. %. No measurable cumyl alcohol (<0.1 wt. %) was found in the cumene product. When desired, the bottoms can be withdrawn, optionally distilled to remove lighter boiling compounds (which can be recycled back to the catalytic distillation reactor) and then optionally diluted with fresh cumene or cumene product and sent to a fixed bed hydrogenation reactor to make additional cumene as illustrated in Illustrative Embodiment III below.

TABLE 3

Catalytic Distillation of 2-Phenyl-2-propanol - Results with Pd-Mordenite Catalyst

| Component | 2-Phenyl-2-propanol Feed | Catalytic Distillation Top Product* |
|---|---|---|
| 2-Phenyl-2-propanol, (wt. %) | 99.2 | <0.1 |
| α-Methyl styrene, (wt. %) | 0.4 | Not Detected |
| Cumene, (wt. %) | 0.1 | >99.6 |
| Isopropylcyclohexane, (wt. %) | 0.1 | <0.2 |
| Cumene Dimer, (wt. %) | <0.1 | Not Detected |
| Other, such as cumene hydroperoxide (wt. %) | 0.2 | <0.1 |

*after removal of water

III. Illustrative Embodiment III (A)—Hydrocracking of Cumene Dimers

The bottom stream from II(B)(i) above was distilled to yield a cumene dimer rich mixture that was diluted with cumene and fed into a fixed bed hydrogenation loaded with the T-366 catalyst as described in II(A)(i) above for hydrocracking under the condition as provided in TABLE 4 below. The results are shown in TABLE 5 below.

TABLE 4

| Feedrate | 33.5 g/hr |
|---|---|
| Reaction Temperature | 260° C. |
| Pressure | 10 bar |
| Hydrogen Flowrate | 4 L/Hr |
| Catalyst Weight | 33.5 g (before reduction) |

TABLE 5

Fixed Bed Cumene Dimer To Cumene Results With T-366 Catalyst At 260° C.

| Component | Cumene dimers in cumene (FEED) | Fixed Bed Product |
|---|---|---|
| 2,3-Dimethyl-2,3-diphenylbutane, (wt %) | 1.94 | 0.05 |
| 2-methyl-2,4-diphenylpentane, (wt %) | 1.03 | 0.09 |
| Cumene, (wt %) | 96.75 | 99.54 |
| Isopropylcyclohexane, (wt %) | 0.08 | 0.18 |
| alpha-Methyl styrene, (wt %) | 0.20 | 0.09 |

III. Illustrative Embodiment III(B)—Hydrocracking of Cumene Dimers

The bottom stream from II(B)(i) above was distilled to yield a cumene dimer rich mixture that was diluted with cumene and fed into a fixed bed hydrogenation loaded with the acidic palladium on H-Mordenite catalyst as described in II(B)(i) above for hydrocracking under the condition as provided in TABLE 6 below. The results are shown in TABLE 7 below.

TABLE 6

| Feed Rate | 33.5 g/hr |
|---|---|
| Reaction Temperature | 220° C. |
| Pressure | 10 bar |
| Hydrogen Flow Rate | 4 L/Hr |
| Catalyst Weight | 33.5 g (before reduction) |

TABLE 7

Fixed Bed Cumene Dimers To Cumene Results
With Palladium On H-Mordenite Catalyst At 220° C.

| Component | Cumene dimers in cumene (FEED) | Fixed Bed Product |
|---|---|---|
| 2,3-Dimethyl-2,3-diphenylbutane, (wt %) | 1.94 | 0.06 |
| 2-methyl-2,4-diphenylpentane, (wt %) | 1.03 | 0.02 |
| Cumene, (wt %) | 96.75 | 99.82 |
| Isopropylcyclohexane, (wt %) | 0.08 | 0.08 |
| alpha-Methyl styrene, (wt %) | 0.20 | 0.02 |

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant inventions defined by the instant specification and claims.

We claim:

1. A process for preparing an alkylene oxide, which process comprises:
   (i) oxidizing an alkylbenzene to obtain a stream comprising alkylbenzene hydroperoxide;
   (ii) contacting at least part of the alkylbenzene hydroperoxide obtained in step (i) with an olefin to obtain a product stream comprising an alkylene oxide;
   (iii) separating alkylene oxide compound from the product stream of step (ii) to obtain (a) a residual product stream comprising alkyiphenyl alcohol and (b) alkylene oxide; and,
   (iv) feeding at least a part of the residual product stream comprising alkylphenyl alcohol to a reactor having a catalytic distillation zone, and concurrently in the reactor:
      (a) contacting the residual product stream comprising alkyphenyl alcohol with hydrogen in the catalytic distillation zone to convert the alkyiphenyl alcohol in the residual product stream to alkylbenzene and form a reaction mixture; and,
      (b) separating alkylbenzene from the reaction mixture by fractional distillation.

2. The process of claim 1, further comprising:
   (v) withdrawing a stream comprising alkylbenzene and having a reduced concentration of alkylphenyl alcohol than the feed stream from the reactor at a position above the catalytic reaction zone;
   (vi) withdrawing from the reactor at a position lower than the catalytic distillation zone a bottom stream comprising dimer(s) of alkylbenzene;
   (vii) converting the dimer(s) of alkylbenzene in the bottom stream from (vi) to alkylbenzene; and,
   (viii) recycling at least a part of the alkylbenzene produced from (v) andlor (vii) to step (i).

3. The process of claim 2, in which in step (vii), the dimer(s) of alkylbenzene is converted to alkylbenzene in the presence of a catalyst comprising a Group VIII metal or a Group IB metal.

4. The process of claim 2, in which the alkyl substituent of the alkylbenzene is a branched alkyl substituent comprising from 3 to 10 carbon atoms.

5. The process of claim 2, in which the alkylbenzene compound is selected from the group consisting of (i) cumene, (ii) para, meta, or ortho-di (isopropyl)benzene, and (iii) a mixture thereof.

6. The process of claim 2, in which at least a part of the alkylbenzene hydroperoxide produced in step (i) is converted to a mixture comprising (a) a phenol compound and (b) a ketone compound.

7. The process of claim 2, in which in step (ii) the alkylbenzene hydroperoxide is contacted with the olefin in the presence of a catalyst comprising a metal selected from the group consisting of Group IVB, Group VB and Group VIB metals.

8. The process of claim 2, in which in step (iv)(a), the residual product stream comprising alkylphenyl alcohol is reacted with hydrogen in the catalytic distillation zone in the presence of a catalyst comprising a group IB metal or a group VIII metal.

9. The process of claim 2, in which in step (iv)(a), less than about 0.5 % by weight of alkylphenyl alcohol is converted to i-propylcyclohexane, and less than about 0.05 % by weight of the alkylbenzene produced is converted to dimer(s) of alkylbenzene.

10. The process according to claim 2, wherein the alkylbenzene compound is ortho, meta, or para-di(isopropyl)benzene or mixtures thereof.

11. The process of claim 1, in which the alkyl substituent of the alkylbenzene is a branched alkyl substituent comprising from 3 to 10 carbon atoms.

12. The process of claim 1, in which the alkylbenzene compound is selected from the group consisting of (i) cumene, (ii) para, meta, or ortho-di (isopropyl)benzene, and (iii) a mixture thereof.

13. The process of claim 1, in which at least a part of the alkylbenzene hydroperoxide produced in step (i) is converted to a mixture comprising (a) a phenol compound and (b) a ketone compound.

14. The process of claim 1, in which in step (ii) the alkylbenzene hydroperoxide is contacted with the olefin in the presence of a catalyst comprising a metal selected from the group consisting of Group IVB, Group YB and Group VIB metals.

15. The process of claim 1, in which in step (iv)(a), the residual product stream comprising alkyiphenyl alcohol is reacted with hydrogen in the catalytic distillation zone in the presence of a catalyst comprising a group IB metal or a group VIII metal.

16. The process of claim 1, in which in step (iv)(a), less than about 0.5 % by weight of alkylphenyl alcohol is converted to i-propylcyclohexane, and less than about 0.05 % by weight of the alkylbenzene produced is converted to dimer(s) of alkylbenzene.

17. The process according to claim 1, wherein the alkylbenzene compound is ortho, meta, or para-di(isopropyl)benzene or mixtures thereof.

18. A process for preparing propylene oxide, which process comprises:
   (i) oxidizing cumene to obtain a stream comprising cumene hydroperoxide;
   (ii) contacting at least part of the cumene hydroperoxide obtained in step (i) with propylene to obtain a product stream comprising propylene oxide;
   (iii) separating propylene oxide compound from the product stream of step (ii) to obtain (a) a residual product stream comprising cumyl alcohol and (b) propylene oxide;

(iv) feeding at least a part of the residual product stream comprising cumyl alcohol to a reactor having a catalytic distillation zone, and concurrently in the reactor:
  (a) contacting the residual product stream comprising cumyl alcohol with hydrogen in the catalytic distillation zone to convert the cumyl alcohol in the residual product stream to cumene and form a reaction mixture; and,
  (b) separating cumene from the reaction mixture by fractional distillation;
(v) withdrawing a stream comprising cumene and having a reduced concentration of cumyl alcohol than the feed stream from the reactor at a position above the catalytic reaction zone;
(vi) withdrawing from the reactor at a position lower than the catalytic distillation zone a bottom stream comprising 2-methyl-2,4-diphenylpentane and dimethyl-2,3-diphenyl-butane;
(vii) converting the 2-methyl-2,4-diphenyl-pentane and dimethyl-2,3-diphenylbutane in the bottom stream from (vi) to cumene; and,
(viii) recycling at least a part of the cumene produced from (v) andlor (vii) to step (i).

19. The process according to claim 18, wherein at least a part of the cumene hydroperoxide produced in step (i) is converted to a mixture comprising (a) a phenol, and (b) a ketone.

20. The process according to claim 18, wherein in step (vii), 2-methyl -2,4-diphenylpentane and dimethyl-2,3-diphenylbutane is converted to cumene in the presence of a catalyst comprising a Group VIII metal or a Group IB metal.

21. The process according to claim 13, wherein in step (vii), 2-methyl -2,4-diphenylpentane and dimethyl-2,3-diphenylbutane is converted to cumene in the presence of a catalyst comprising a metal selected from the group consisting of copper, palladium, platinum and nickel.

22. The process according to claim 18, wherein in step (iv)(a), the residual product stream comprising cumyl alcohol is reacted with hydrogen in the catalytic distillation zone in the presence of a catalyst comprising a group IB metal or a group VIII metal.

23. The process as described in claim 18 wherein in step (iv)(a), less than about 0.5 % by weight of cumyl alcohol is converted to i-propylcyclohexane, and less than about 0.05 % by weight of cumene produced is converted to 2-methyl-2,4-diphenylpentane and dimethyl-2,3-diphenylbutane.

* * * * *